United States Patent [19]
Ishizuka et al.

[11] Patent Number: 5,098,935
[45] Date of Patent: Mar. 24, 1992

[54] CARCINOSTATIC OR ANTITUMOR ANTIBIOTIC, CONAGENIN, AND PRODUCTION AND USES THEREOF

[75] Inventors: Masaaki Ishizuka, Mishima; Takashi Yamashita, Numazu; Hiroshi Naganawa, Tokyo; Hironobu Iinuma, Wako; Kunio Isshiki, Fujisawa; Masa Hamada, Naito; Kenji Maeda; Tomio Takeuchi, both of Tokyo, all of Japan

[73] Assignees: Zaidan Hojin Biseibutsu Kagaku Kenkyu Kai; Kanegafuchi Kagaku Kogyo Kabushiki Kaisha, both of Japan

[21] Appl. No.: 524,576

[22] Filed: May 17, 1990

[30] Foreign Application Priority Data

May 23, 1989 [JP] Japan ................................. 1-127846

[51] Int. Cl.$^5$ ............................................ A61K 31/195
[52] U.S. Cl. .................... 514/563; 435/106; 435/253.5; 562/567
[58] Field of Search ................. 562/567; 514/551, 563

[56] References Cited

U.S. PATENT DOCUMENTS 2,856,421 10/1958 Hasbrouck .......................... 562/567
3,856,854 12/1974 Schnettler ........................... 562/567

*Primary Examiner*—Michael L. Shippen
*Attorney, Agent, or Firm*—Lalos & Keegan

[57] ABSTRACT

A new antibiotic, named Conagenin, is provided which can exhibit useful carcinostatic or antitumor activities on carcinomas and tumors, particularly malignant tumors, of mammalian animals including man. Conagenin can be produced by fermentation of microorganisms of genus Streptomyces, typically *Streptomyces roseosporus* MI696-AF3 strain identified under the deposit number FERM BP-2738. Conagenin has formula (I) and is useful for medicinal purposes, particularly as carcinostatic agent or antitumor agent for inhibiting carcinomas and malignant tumors of mammalian animals, including man.

4 Claims, 2 Drawing Sheets

CARCINOSTATIC OR ANTITUMOR ANTIBIOTIC, CONAGENIN, AND PRODUCTION AND USES THEREOF

FIELD OF THE INVENTION

This invention relates to a new antibiotic, Conagenin, which exhibits a useful carcinostatic or antitumor activity and a process for the production thereof. This invention also relates to a pharmaceutical composition containing Conagenin as active ingredient which is useful as carcinostatic or antitumor agent and a method of inhibitingly treating carcinomas or tumors, particularly malignant tumors of mammalian animals including man therewith. This invention also includes a mew microorganism which is useful for the production of the new antibiotic Conagenin.

BACKGROUND OF THE INVENTION

There are about 5,000 different antibiotics produced by microorganisms which have already been reported in the art, some of which have been used widely for the therapeutic treatments of carcinomas, tumors and other infections. Among metabolites of microorganisms belonging to the genus Streptomyces, actinomycin D, mitomycin C, bleomycin, daunomycin, adriamycin and acracinomycin are typical as those having been used as carcinostatic and antitumor agents.

Nevertheless, it has always been demanded still further to discover or produce new carcinostatic or antitumor substances having a unique carcinostatic or antitumor activity which is different in mechanism of function from known, conventional carcinostatic or antitumor antibiotics and having a low toxicity and thus being capable of using for the therapeutic treatment of carcinomas and malignant tumors of man.

Accordingly, a main object of this invention is to provide a new carcinostatic or antitumor antibiotic, Conagenin.

Another object of this invention is to provide a process for the production of Conagenin.

A further objection of this invention is to provide a pharmaceutical composition containing Conagenin as active ingredient.

A yet further object of this invention is to provide a method of inhibitingly treating carcinomas or malignant tumors of mammalian animals including man with Conagenin.

A still further object of this invention is to provide a new microorganism which can produce Conagenin.

SUMMARY OF THE INVENTION

According to a first aspect of this invention, therefore, there is provided a new antibiotic, Conagenin, represented by the formula:

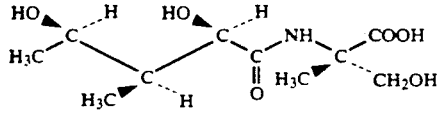

and a salt thereof.

Typical examples of salts of Conagenin include metal salts at the carboxyl group of Conagenin, particularly alkali metal salts such as sodium and potassium salts and alkaline earth metal salts such as calcium salts.

BRIEF EXPLANATION OF THE ATTACHED DRAWINGS

DETAILED DESCRIPTION OF THE INVENTION

Conagenin is a new antibiotic substance that we, the present inventors, have now discovered as a result of our study on such substances which are active to increase binding of concanavalin A to the carcinoma cell membrane, with our intention of obtaining a useful carcinostatic substance which can exhibit its carcinostatic or antitumor activity through it nature of modifying the carcinoma cell membrane. We have found that Conagenin can exhibit a significant carcinostatic or antitumor activity in vivo, for example against Ehrlich's solid carcinoma in mice, with a low toxicity.

Typical physico-chemical properties of Conagenin are as follows:

(1) Appearance: Colorless plate crystals (2) Elemental analysis: C, 47.96%; H, 7.67%; N, 5.64%; O, 38.19%

(3) Mass spectrum: m/z 250.1291$(M+H)^+$ (by FAB high resolution mass spectrometry)

(4) Molecular formula: $C_{10}H_{19}NO_6$ (5) Melting point: 159°–161° C.

(6) Specific rotation: $[\alpha]_D^{27} + 55.4°$ (c 1.0, methanol)

(7) Solubility: Easily soluble in methanol; soluble in water; but sparingly soluble in chloroform.

(8) UV absorption spectrum (in methanol): Terminal absorption is observed.

Figure 1:
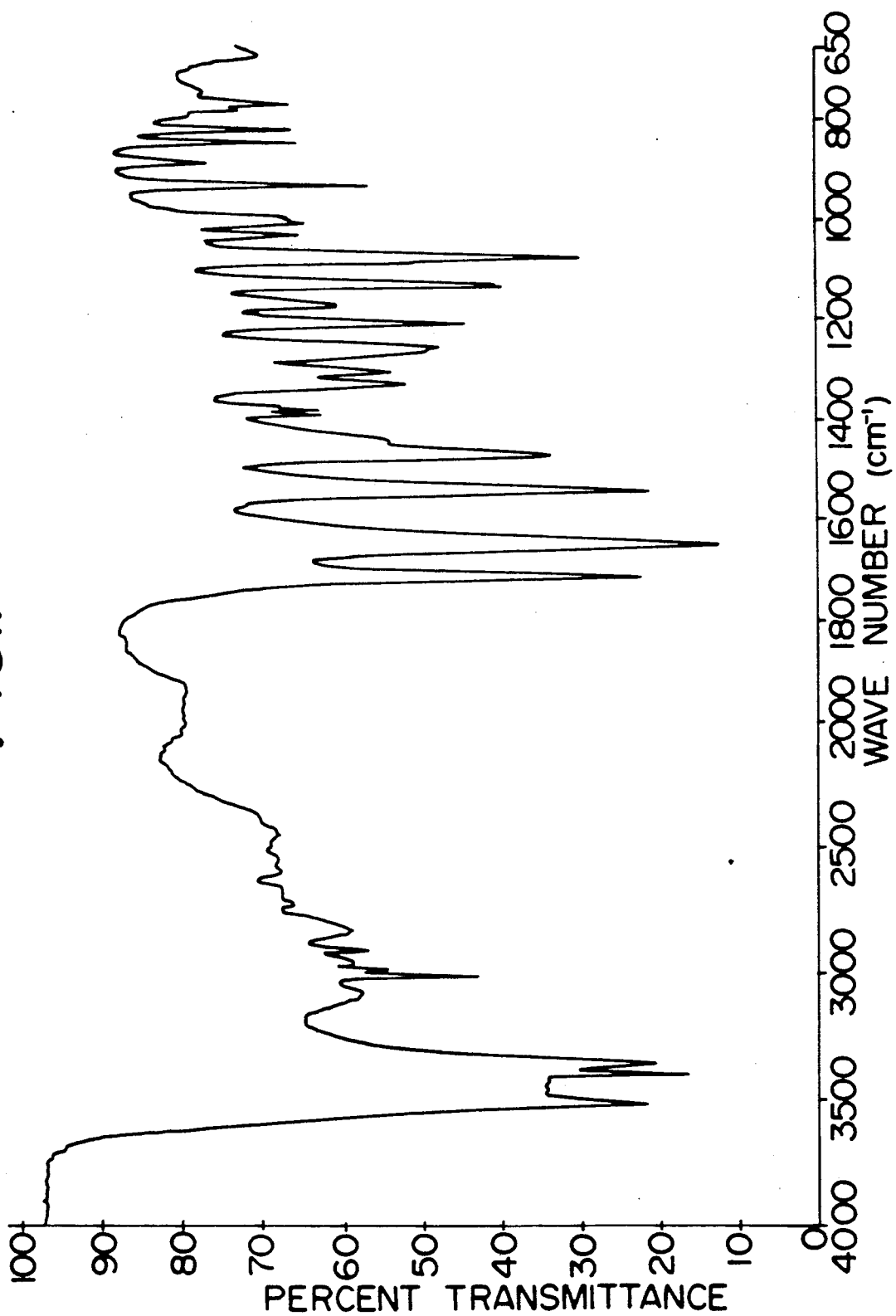
FIG. 1 is an infrared absorption spectrum of Conagenin pelleted in KBr tablet, in which the abscissa axis represents wave number ($cm^{-1}$) and the ordinate axis represents transmittance (%).

(9) IR absorption spectrum (KBr): Shown in FIG. 1 of the appended drawings.

Figure 2:
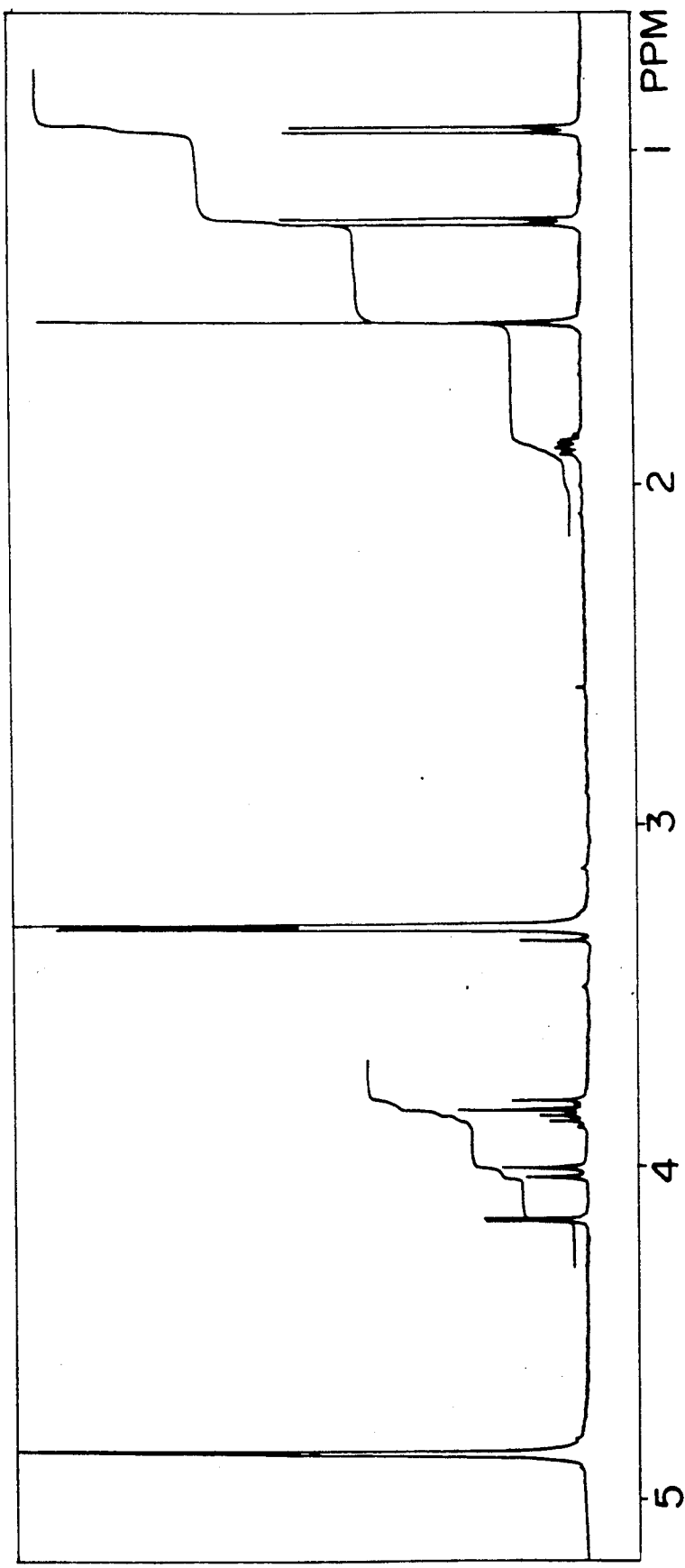
FIG. 2 is a proton nuclear magnetic resonance spectrum of Conagenin in deuteromethanol, in which the abscissa represents chemical shift (ppm) and tetramethylsilane was used as internal standard.

(10) NMR spectra:

(a) $^1H$ NMR spectrum in deuteromethanol is shown as chemical shift (ppm) in FIG. 2 of the appended drawings.

(b) $^{13}C$ NMR spectrum in deuteromethanol is shown as chemical shift (ppm) in Table 1 given below.

TABLE 1

| | | | | |
|---|---|---|---|---|
| 176.7s | 175.8s | 75.3d | 71.2d | 66.2t |
| 62.7s | 43.7d | 21.2q | 20.0q | 8.3q |

Note:
s: singlet; d: doublet; t: triplet; q: quartet
Internal standard: Tetramethylsilane On the basis of the above-shown various spectra and X-ray diffraction analysis, Conagenin has been determined to have the chemical structure of formula (I) above. Since no such compound that the structure thereof conforms to that of formula (I) has been reported yet, Conagenin is, we decided, to be a new antibiotic.

According to a second aspect of this invention, there is provided a process for the production of an antibiotic, Conagenin, which comprises cultivating a Conagenin-producing strain of the genus Streptomyces in a culture medium until a substantial amount of Conagenin is produced and accumulated in the culture, and then recovering Conagenin from the resulting culture.

One typical example of Conagenin-producing strains of the genus Streptomyces to be used in the process of the second aspect of this invention is a new strain of Actinomycetes which was isolated from soil samples collected in Zushi, Kanagawa prefecture, Japan in February, 1988 and to which MI696-AF3 was assigned. The subject strain MI696-AF3, was deposited under the Budapest Treaty at the Fermentation Research Institute, Agency of Industrial Science and Technology located at 1-3 Higashi 1-chome Tsukuba-shi Ibaraki-ken, Japan (305) on Mar. 2, 1989 under the deposit number FERM BP-2738. The microbiological properties of MI696-AF3 strain are shown below:

1. Morphology

Microscopic observation shows that MI696-AF3 strain develops aerial hyphae from branched substrate mycelia and that the aerial hyphae are relatively long and straight in shape with no formation of spirals and whirls. At the tip of the aerial hyphae a chain of more than 50 spores is observed. The size of each spore is about $0.6 \times 1.0$–$1.2$ microns and the surface of the spores is smooth.

2. Growth Characteristics In Various Culture Media

The standard given in each of the brackets [ ] for the description of color is of "Color Harmony Manual" of Container Corporation of America.

(1) Sucrose-nitrate-agar medium (cultured at 27° C.)

White to pinkish white aerial hyphae are thinly formed on the colorless growth. No soluble pigment is observed.

(2) Glucose-asparagine-agar medium (culture at 27° C.)

The growth is pale yellow in color and the aerial hyphae show white to pinkish white [3 ca, Pearl Pink] in color. No soluble pigment is observed.

(3) Glycerin-asparagine-agar medium (ISP-medium 5, cultured at 27° C.)

Aerial hyphae of pinkish white to pale pink [4 ca, Flesh Pink] in color are formed on the growth of pale yellowish brown [3 ie, Camel] to yellowish brown [3 le, Cinnamon] in color and the soluble pigment is yellowish brown.

(4) Starch-inorganic salt-agar medium (ISP-medium 4, cultured at 27° C.)

Aerial hyphae of pale pink [4 ca, Flesh Pink] in color are formed on the growth of pale yellow [2 ea, Lt Wheat] to pale yellowish brown [2 ic, Honey Gold] in color. No soluble pigment is observed.

(5) Tyrosine-agar medium (ISP-medium 7, cultured at 27° C.)

The growth is pale yellow [2 ea, Lt Wheat] to pale yellow brown [2 ic, Honey Gold] in color and the aerial hyphae show brownish white [3 ca, Pearl Pink] in color. No soluble pigment is observed.

(6) Nutrient agar medium (cultured at 27° C.)

The growth is colorless without formation of aerial hyphae thereon. No soluble pigment is observed.

(7) Yeast-malt agar medium (ISP-medium 2, cultured at 27° C.)

Aerial hyphae of pale pink [4 ca, Flesh Pink to 5 ca, Flesh Pink] in color are formed on the growth, of pale yellowish brown [2 ic, Honey Gold to 3 le, Cinnamon] in color. No soluble pigment is observed.

(8) Oatmeal agar medium (ISP-medium 3, cultured at 27° C.)

The growth is colorless and the aerial hyphae is pinkish white to pale pink [4 ca, Flesh Pink to 5 ca, Flesh Pink] in color. No soluble pigment is observed.

(9) Glycerin-nitrate-agar medium (cultured at 27° C.)

Aerial hyphae of brownish white [3 ca, Pearl Pink] in color are formed on the growth of pale yellow [1½ ea, Lt Yellow] to yellowish brown [3 ng, Yellow Maple] in color. A little of soluble pigment of yellowish brown color is observed.

(10) Starch agar medium (cultured at 27° C.)

The growth is pale yellow to pale yellowish brown [2 gc, Bamboo] in color and the aerial hyphae is pale pink [4 ca, Flesh Pink] in color. No soluble pigment is observed.

(11) Calcium malate-agar medium (cultured at 27° C.)

White aerial hyphae are formed on the colorless growth. No soluble pigment is observed.

(12) Cellulose (synthetic test solution containing filter paper pieces, cultured at 27° C.)

White aerial hyphae are thinly formed on the colorless growth. No soluble pigment is observed.

(13) Gelatin stab

In both a 15% simple gelatin culture medium (cultured at 20° C.) and a glucose-peptone-gelatin culture medium (cultured at 27° C.), the growth is colorless without formation of aerial hyphae. No soluble pigment is observed.

(14) Skimmed milk (cultured at 37° C.)

The growth is colorless without formation of aerial hyphae. The soluble pigment is slightly brown tinged.

3. Physiological Properties (1) Temperature range for the growing

In the tests which were conducted on a starch-yeast-agar medium comprising 1% of soluble starch, 0.2% of yeast extract (a product of Nippon Pharmaceutical Co., Ltd.) and 3.0% of stringe agar and having pH of b 7.0 to 7.2 at varying temperatures, namely 20° C., 24° C., 27° C., 30° C., 37° C. and 50° C., the growing of the strain occurred at any of temperatures tested except at 50° C. It appears that the optimum growth temperature is in the range of 30° C. to 37° C.

(2) Liquefaction of gelatin (in 15% simple gelatin medium, cultured at 20° C.; and in glucose-peptone-gelatin medium, cultured at 27° C.)

Liquefaction was started at about 7th day of the incubation in the simple gelatin medium and at about 11th day of the incubation in the glucose-peptone-gelatin medium. The grade of liquefaction is medium or rather stronger in the former and is slow and medium in the latter.

(3) Hydrolysis of starch (starch-inorganic salt agar medium and starch-agar medium, cultured at 27° C. in both the cases)

Hydrolysis was observed to have been started at about 3rd day of the incubation in both the media, where the grade of hydrolysis is rather strong.

(4) Coagulation and peptonization of skimmed milk (skimmed milk, cultured at 37° C.)

Peptonization was started at about 8th day of incubation with no occurrence of coagulation. The progress of coagulation is slow and completed in the 3rd week from the start thereof.

(5) Formation of melanoid pigment (trypton-yeast broth, ISP-medium 1; peptone-yeast-iron agar medium, ISP-medium 6; tyrosine-agar medium, ISP-medium 7; each cultured at 27° C.)

The melanoidformation was negative in each of the culture media tested.

(6) Utilization of various carbon sources (Pridham-Gottlieb agar medium, ISP-medium 9, cultured at 27° C.)

D-glucose, L-arabinose, D-xylose, rhamnose and lactose were well utilizable for the growth. Inositol, D-fructose, sucrose, D-mannitol and raffinose were not utilizable.

(7) Liquefaction of calcium malate (calcium malate agar medium, cultured at 27° C.)

The liquefaction was positive.

(8) Reduction of nitrate (aqueous peptone solution containing 0.1% potassium nitrate, ISP-medium 8, cultured at 27° C.)

The reduction was positive.

(9) Decomposition of cellulose (synthetic test solution containing filter paper pieces added, cultured at 27° C.)

The decomposition was negative.

Summarizing the microbiological properties given above, the MI696-AF3 strain is morphologically characterized in that the aerial hyphae are straight in shape with no formation of spirals and whirls, and that the spore surface is smooth. In various culture media, aerial hyphae of pinkish white to pale pink in color ar formed on the vegetable mycelium of colorless or of pale yellow to pale yellowish brown in color and no soluble pigment is produced in rather many cases, but sometimes such soluble pigment as slight brown tinged is observed. The formation of melanoid pigment is negative in any of trypton-yeast broth, peptone-yeast-iron agar and tyrosine-agar media. The grade of protein-decomposing activity is medium to strong and that of starch-decomposing activity is also strong. 2,6-Diaminopimelic acid present in the cell wall was of the LL-type.

In view of the microbiological properties described above, we have judged that the MI696-AF3 strain belongs to the genus Streptomyces. Then, the search of analogous known species with reference to the properties of the MI696-AF3 strain revealed *Streptomyces roseofulvus* [Literature 1, "International Journal of Systematic Bacteriology", Vol. 18, p. 165 (1968); Literature 2, "International Journal of Systematic Bacteriology", Vol. 30, P. 399 (1980)] and *Streptomyces roseosporus* [Literature "International Journal of Systematic Bacteriology", Vol. 18, P. 370 (1968)]as being the most analogous known strains. Thus, comparison was made on the properties between the MI696-AF3 strain and the two known strains, *Streptomyces roseofluvus* and *Streptomyces roseosporus* as summarized in Table 2 below.

TABLE 2

|  | MI696-AF3 | Streptomyces roseosporus IMC S-0143 (ISP5122) | Streptomyces roseofluvus IMC S-0243 (ISP5172) |
|---|---|---|---|
| Nature of aerial hyphae | Straight | Straight | Straight |
| Spore surface | Smooth | Smooth | Smooth |
| Color or aerial hyphae | Pinkish white to pale pink | Pinkish white to pale pink | Pinkish white to pale pink |
| Color of growth | Colorless or pale yellow to pale yellowish brown | Colorless or pale yellow to pale yellowish brown | Colorless or pale yellow to pale yellowish brown |
| Soluble pigment | None (sometimes yellowish brown) | None (sometimes yellowish brown) | None or yellow tinged |
| Formation of melanoids | | | |
| In ISP-medium 1 | − | − | − |
| In ISP-medium 6 | − | − | − |
| In ISP-medium 7 | − | − | − |
| Hydrolysis of starch | +++ | +++ | +++ |
| Coagulation of skimmed milk | − | − | − |
| Peptonization of skimmed milk | +++ | ++± | ++ |
| Liquefaction of gelatin | | | |
| In simple gelatin | ++ | ++ | +++ |
| In glucose-peptone-gelatin | +± | + | ± |
| Reduction of nitrate | + | + | + |
| Utilization of carbon sources* | | Lit. 1 | Lit. 2 |
| D-glucose | + | + | + + + |
| L-arabinose | + | + | + + + |
| D-xylose | + | + | + + + |
| D-fructose | − | − | ? + + |
| Sucrose | − | − | − + + |
| Inositol | − | − | − − − |
| Rhamnose | + | + | + + + |
| Raffinose | − | − | − + + |
| D-mannitol | − | − | − − − |
| Lactose | + | + | + |

Utilization of carbon sources*
+means "utilizable"; ? means "divergent results"; −means "not utilizable".
Lit.1: International Journal of Systematic Bacteriology, 18, 165 (1968)
Lit.2: International Journal of Systematic Bacteriology, 18, 370 (1968)

As can be seen from Table 2 above, the MI696-AF3 strain closely resembles to both the species, *Streptomyces roseoporus* and *Streptomyces roseofluvus*. However, the MI696-AF3 strain is distinguished from *Streptomyces roseofluvus* in the utilization of D-fructose, sucrose and raffinose and in the soluble pigment. On the other hand, the MI696-AF3 strain and *Steptomyces roseosporus* are closely similar in all the properties tested. Thus, the MI696-AF3 strain has now been identified as *Streptomyces roseosporus* MI696-AF3.

The strain MI696-AF3 has been deposited in the Japanese depository "Fermentation Research Institute", Agency of Industrial Science and Technology (located in Tsukuba-shi, Ibaraki-ken, Japan), since 2nd March, 1989 under the deposit number "FERM P-10598" and now deposited under the deposit number "FERM BP-2738" in terms of the Budapest Treaty.

As already mentioned briefly, Conagenin can exhibit a significant carcinostatic or antitimor activity with a low toxicity. Such useful biological properties of Conagenin have been confirmed experimentally by us, some of which are given below.

(1) Toxicity

Toxicity of Conagenin was tested by intraperitoneal administration to female ICR mice and estimated as its $LD_{50}$ being higher than 50 mg/Kg.

(2) Inhibitory activity on Ehrlich's solid carcinoma in mice ICR mice (female, 6 weeks-aged, 4 mice in each group) were inoculated with Ehrlich's ascites carcinoma cells ($2 \times 10^6$ per mouse in the form of a cell suspension) subcutaneously at the groin of the mice. After the 7th day from the inoculation of the carcinoma cells, an injectable solution of Conagenin was intraperitoneally injected into the carcinoma-bearing mice at a dosage of 6.25, 3.1, 1.56, 0.78, 0.39 and 0.195 mg/Kg once a day during the consecutive 7 days for each group of mice. On the 15th day from the inoculation of the carcinoma cells, the solid carcinoma so grown was cut off and the weight of the solid carcinoma was determined. Control test was conducted using 8 mice of the same type as above in a usual manner. Percent inhibition of the proliferation of the solid carcinoma, i.e. the percent decrease in the weight of the solid carcinoma in each treated group of mice administered with Conagenin as compared to that in the control group of mice (untreated), is callculated and shown in Table 3 below.

TABLE 3

| Dosage of Conagenin (mg/Kg/day) | Percent inhibition (%) |
|---|---|
| 6.25 | 45 |
| 3.1 | 67 |
| 1.56 | 44 |
| 0.78 | 58 |
| 0.39 | 29 |
| 0.195 | 44 |

(3) Effect of Conagenin on the surface of carcinoma cell membrane

Leukemia L1210 cells were suspended in a 10% bovine serum-added minimum essential medium [MEM, a product of Nissui Pharmaceutical Co., Ltd.] to give a concentration of $2 \times 10^5$ cells/ml and Conagenin was added to the cell suspension so that the cell suspensions had a Conagenin concentration of 1 μg/ml, 0.5 μg/ml and 0.25 μg/ml, respectively. Each of the resulting suspensions was incubated in a $CO_2$-incubator ($CO_2$ concentration:5%) at 37° C. for 2 days. A radioisotope-labelled Concanavalin A (Concanavalin A N-[acetyl-$^3$H] acetylated; a product of Amersham Co., Ltd.) in an amount of 40 nCi/ml was added to the suspension under incubation at a time of one hour before the end of the incubation. The incubated cells were fixed on a filter paper by a cell harvester and the radioactivity value of the cells so fixed was measured by a liquid scintillation counter. The respective values thus given were converted assumed that the radioactivity value of the control group sample was amounting to 100, and the converted values are shown in Table 4 as the increase in binding of Concanavalin A to L1210 cells. As is clear from Table 4, Conagenin could increase the binding of Concanavalin A to L1210 cells.

TABLE 4

| Concentration of Conagenin (μg/ml) | Increase in binding of Concanavalin A |
|---|---|
| 1.0 | 121 |
| 0.5 | 129 |
| 0.25 | <100 |

On the basis of such useful biological properties of Conagenin as given above, a third aspect of this invention is a pharmaceutical composition comprising as active ingredient an antibiotic, Conagenin having formula (I) above, in combination with a pharmaceutically acceptable carrier or carriers for the active ingredient. The pharmaceutical composition according to this invention is effective and useful as carcinostatic or antitumor agent for mammalian animals, including man.

The pharmaceutical composition according to this invention may be formulated in a conventional manner into any convenient form of medicinal preparations for oral, intraperitoneal or parenteral administration such as, for example, injections, tablets, capsules, granules, syrups, suppositories and ointments. As pharmaceutically acceptable carriers, there may be used any of known, conventional ones as desired. The nature and composition of carriers to be used may vary depending on the route and manner of administration and include organic and inorganic, solid and liquid, usually inert carriers and excepients known and available for pharmaceutical purposes. Some concrete examples of such carriers are crystalline cellulose, gelatin, lactose, starch magnesium stearate, talc, vegetable and animal fats and oils, gums and polyalkylene glycols among others. The concentration of the active carcinostatic or antitumor ingredient, Conagenin, in the pharmaceutical composition of this invention may vary from 0.2 to 100% by weight, preferably from 1 to 90% by weight, based on the total weight of the composition. If desired, the pharmaceutical composition of this invention may contain, in addition to Conagenin, one or more other pharmacologically active ingredients including those having carcinostatic, antitumor and other pharmacological activities.

The pharmaceutical composition according to this invention may be administered at a dosage capable of exhibiting a desired pharmacological activity without being accompanying with any appreciable side effect. Particular dosage is to be chosen by a medical man in each particular case, but the dosage of the active ingredient, conagenin, will in general be a level in the range of 10 mg-10 g, preferably 20 mg-5 g, per day on adult patient for therapeutic treatments of carcinomas and malignant tumors. In these cases, the pharmaceutical composition of this invention may conveniently be administered as a unit preparation containing 1 mg-5 g, preferably 3 mg-1 g of the active ingredient Conagenin.

Thus, according to a fourth aspect of this invention, there is provided a method of inhibitingly treating carcinomas or malignant tumors of mammalian animals, including man, which comprises administering an antibiotic Conagenin having formula (I) above, usually in the form of a pharmaceutical composition, in a therapeutically effective amount to a mammalian animal having a carcinoma or malignant tumor.

As already mentioned briefly, the dosage of Conagenin may suitably be determined by a medical man, typically with having regard to the age, body weight, sympton of patients and therapeutic purpose as intended. The effective dosage as indicated above can be administered continuously or intermittenlly as long as the total dosage does not exceed such a specific level as decided in view of results of animal tests and various circumstances.

The fermentative production of Conagenin of this invention is now described.

In carrying out the process for the production of Conagenin according to the second aspect of this invention, a Conagenin-producing strain, preferably Streptomyces roseosporus MI696-AF3 strain (identified as the culture deposited under FERM BP-2738), is cultivated by a known and ordinary method for the cultivation of microorganisms of Actinomyces. Conagenin is produced and accumulated predominantly in the liquid phase of the culture broth. In this process, it is preferably that Conagenin is produced by cultivating the MI696-AF3 strain in a suitable culture medium under appropriate conditions. The culture medium used for the cultivation may contain assimilable carbon sources, assimilable nitrogen sources and inorganic salts, etc. which are customarily used for the cultivation of Actinomyces. The available carbon sources include those known materials such as mannose, glucose, galactose, maltose, peptone, dextrin, starch, millet, mollasses and soybean oils. The available nitrogen sources include those known materials such as soybean powder, meat extract, peptone, yeast extract, dried yeast, NZ-amine, nitrate, ammonium nitrate, ammonium sulfate and others. The inorganic salts may include sodium chloride, phosphates, calcium carbonate, magnesium sulfate, copper sulfate, iron sulfate, manganese chloride, zinc sulfate and other.

The productive culture medium which may be used for commercial production of Conagenin may contain meat extract, peptone, yeast extract and some inorganic salts and, if desired, an anti-foaming agent such as animal oils, vegetable oils, etc. Further, any other organic and inorganic materials which are known as the ones used for activation of a microorganism of Actinomyces and are useful for the production of Conagenin may also advantageously be incorporated into the culture medium.

The cultivation of the MI696-AF3 strain for the production of Conagenin may be conducted under aerobic conditions and preferably under submerged conditions. The cultivation of the Conagenin-producing strain may be effected in a range of temperatures where said strain can grow and produce a substantial amount of Conagenin, and the MI696-AF3 strain may be cultivated at a temperature of 25° to 40° C., preferably at a temperature of 30° to 37° C. The other conditions for the cultivation may suitably be chosen, depending on and according to the microbiological and physiological properties of the Conagenin-producing strain as employed.

In general, the recovery of Conagenin from the culture of the Conagenin-producing microorganism may be achieved with utilizing that Conagenin is a weakly acidic substance and is readily soluble in methanol, soluble in water but is insoluble in some organic solvent such as chloroform. Principally, it is preferred that the recovery of Conagenin from the culture of the Conagenin-producing microorganism is conducted by the following procedure. Thus, the culture obtained or the culture broth is filtered or centrifuged to remove the incubated cells of the microorganism, and the broth filtrate is mixed with activated carbon for adsorption of the active substance thereon. The activated carbon containing the adsorbed Conagenin therein is then extracted with 50% aqueous acetone. The resulting extract containing Conagenin is then concentrated under a reduced pressure to dryness, and the residue is dissolved in water, followed by extraction of the resulting aqueous solution with n-butanol. The extract in n-butanol is then again concentrated to dryness under a reduced pressure to give a residue comprising Conagenin. This crude product may then be partially purified by a silica gel column chromatography as developed with a mixed solvent of butyl acetate, n-butanol and water as eluent. Further purification of a partially pure product of Conagenin may be effected by a high performance liquid chromatography on a revese phase column of a silylated silica gel and using a gradient elution method with 10% aqueous methanol to 100% methanol, so that the active fractions of the effluent containing only Conagenin as the active substance may be obtained. When a pure solution of Conagenin in methanol is concentrated under a reduced pressure, Conagenin may be precipitated in the form of colorless crystals.

This invention further provides, as a fifth aspect thereof, a new microorganism, Streptomyces roseosporus MI696-AF3 strain, which is identified as the culture deposited under the deposit number FERM BP-2738 in the "Fermentation Research Institute" and which is characterized by being capable of producing an antibiotic, Conagenin, which is a compound having formula (I) given above.

The following Example illustrates a typical process for the production of Conagenin, but it does not limit this invention thereto.

EXAMPLE

A loopful amount of Streptomyces roseosporus MI696-AF3 strain (identified as FERM BP-2738) was taken from its agar slant culture and inoculated into 110 ml-portions of a liquid medium (pH 7.4) containing 2.0% galactose, 2.0% dextrin, 1.0% soy-peptone (sold under Bactosoytion by Difco Co.), 0.5% corn steep liquor (a product of Japan Maize Products Co., Lt.), 0.2% ammonium sulfate, 0.2% calcium carbonate and 0.03% antifoaming silicone oil (sold under Silicone KM70 by Shin-Etsu Chemical Co., Ltd.), of which each 100-ml portion had been placed in each of two Erlenmyer flasks filled with waffle. Each inoculated medium so prepared was cultivated under shaking at 27° C. for 3 days. The seed culture thus obtained was inoculated in 3 ml-portions each into 110 ml-portions of a liquid culture medium comprising 2.0% maltose (a product of Hayashibara Biochemical Co., Ltd.), 0.5% meat extract for cultivation of bacteria (a product of Kyokuto Pharmaceutical Co., Ltd.), 0.5% peptone (polypeptone available from Nippon Pharmaceutical Co., Ltd.), 0.3% powdery yeast extract S (a product of Nippon Pharmaceutical Co., Ltd.), 0.3% sodium chloride and 0.1% magnesium sulfate ($7H_2O$) as well as inorganic salts as incorporated in the form of 1.25 ml/l of a solution of 2.8 g of cupric sulfate ($5H_2O$), 0.4 g of ferrous sulfate, 3.2 g of manganese chloride ($4H_2O$) and 0.8 g of zinc sulfate ($7H_2O$) in 500 ml of distilled water, with each 110 ml-portion portion of said liquid culture medium being placed in each of 91 Erlenmyer flasks fitted with waffle. Each inoculated culture medium so obtained was incubated under shaking at 27° C. for 4 days. The resulting culture broth was filtered to recover the culture broth filtrate. To the filtrate (8100 ml) was added activated carbon 200 g, followed by filtration. The active ingredient substance thus adsorbed on the activated carbon was extracted with 4 l of 50% aqueous acetone and the resulting extract was concentrated in vacuo. The concentrated residue was dissolved in 2 l of distilled water and the aqueous solution was extracted with the same volume of butanol at pH of 3. the butanol extract, after adjustment of the pH to 8, was concentrated in vacuo to yield 7.5 g of a brown oil.

The oil so obtained was subjected to chromatography on a silica gel column (150 ml) using butyl acetate-butanol-acetic acid-water (6:4:1:1 by volume) as eluent. The resulting eluate was fractionated in a usual manner and there were collected such eluate fractions which showed Rf values of 0.50–0.55 on a silica gel thin layer chromatography [Art. 5715 silica gel plate made of Merck Co., eluent:butanol-acetic acid-water (4:1:1 by volume)] and which developed color with ninhydrine. The fractions so collected were concentrated in vacuo, affording 1.2 g of crude Conagenin product.

The crude product was subjected to high performance liquid chromatography (Senshu Pack Nucleosil 5C$_{18}$, 20 ϕ×300 mm, a product of Senshu Kagaku Co., Japan) at a flow rate of 5 ml/min with gradient elution such that the mobil phase is gradually changed from 10% aqueous methanol to 100% methanol during the period of 20 minutes, followed by elution with pure (100%) methanol for further 20 minutes. The effluents showing the peak over the period of 21 minutes, were fractionated and collected and the collected fractions were concentrated in vacuo, affording 34.8 mg of Conagenin as colorless crystals. A methanol solution of this crystalline substance gave a single spot on a silica gel thin chromatography [Art. 5715 silica gel, a product of Merck Co.] using butanol-acetic acid-water (4:1:1 by volume) as the developer. Apparently, this can suggest that the product finally obtained was a pure Conagenin.

We claim:

1. A compound having the formula:

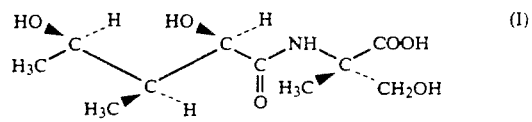

or an alkali metal or alkaline earth metal salt thereof.

2. A pharmaceutical composition comprising as active ingredient the compound of formula (I) as defined in claim 1, in an amount sufficient to act as a carcinostatic agent or antitumor agent and in combination with a pharmaceutically acceptable carrier or carriers for the active ingredient.

3. The composition of claim 2 wherein said amount is at least 0.2% by weight of the total composition.

4. The composition of claim 2 wherein the amount is 1–90% by weight of the total composition.

* * * * *